United States Patent
Baynham et al.

(10) Patent No.: US 7,481,829 B2
(45) Date of Patent: Jan. 27, 2009

(54) BONE FIXATION PLATE

(75) Inventors: Bret O'Neil Baynham, Jupiter, FL (US);
G. Clay Baynham, Jupiter, FL (US);
Matthew G. Baynham, Jupiter, FL (US); David Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 418 days.

(21) Appl. No.: 10/419,686

(22) Filed: Apr. 21, 2003

(65) Prior Publication Data
US 2004/0210217 A1 Oct. 21, 2004

(51) Int. Cl.
*A61B 17/80* (2006.01)
*A61B 17/04* (2006.01)
*A61F 2/08* (2006.01)

(52) U.S. Cl. .................. 606/289; 606/323; 606/327

(58) Field of Classification Search ........... 606/61, 606/69–71, 73
See application file for complete search history.

(56) References Cited

U.S. PATENT DOCUMENTS

| | | | |
|---|---|---|---|
| 4,013,071 A | 3/1977 | Rosenberg | |
| 4,611,581 A | 9/1986 | Steffee | |
| 4,716,893 A * | 1/1988 | Fischer et al. | 606/66 |
| 5,261,911 A | 11/1993 | Carl | |
| 5,569,251 A | 10/1996 | Baker et al. | |
| 5,578,034 A | 11/1996 | Estes | |
| 5,584,832 A | 12/1996 | Schlapfer | |
| 5,603,713 A | 2/1997 | Aust et al. | |
| 5,607,426 A | 3/1997 | Ralph et al. | |
| 5,624,441 A | 4/1997 | Sherman et al. | |
| 5,643,260 A * | 7/1997 | Doherty | 606/61 |
| 5,688,273 A | 11/1997 | Errico et al. | |
| 5,713,900 A | 2/1998 | Benzel et al. | |
| 5,752,957 A | 5/1998 | Ralph et al. | |
| 5,810,818 A | 9/1998 | Errico et al. | |
| 5,843,082 A | 12/1998 | Yuan et al. | |
| 5,885,286 A | 3/1999 | Sherman et al. | |
| 5,951,558 A | 9/1999 | Fiz | |
| 6,045,552 A | 4/2000 | Zucherman et al. | |
| 6,139,550 A | 10/2000 | Michelson | |
| 6,193,720 B1 | 2/2001 | Yuan et al. | |
| 6,224,602 B1 | 5/2001 | Hayes | |
| 6,231,610 B1 | 5/2001 | Geisler | |
| 6,235,034 B1 * | 5/2001 | Bray | 606/71 |

(Continued)

FOREIGN PATENT DOCUMENTS

EP 0 613 664 A2 12/1993

*Primary Examiner*—Anu Ramana
(74) *Attorney, Agent, or Firm*—McHale & Slavin, P.A.

(57) ABSTRACT

A bone plate for use in anterior lumbar spinal fixation has interlocking components to prevent dislodgement of the plate due to anatomical forces. The exposed surface of the plate is smooth to prevent trauma to internal body tissue. The plate spans the intervertebral space with each end attached to an adjacent vertebrae by locking screws threadably engaged with tubular bone anchors. The bone anchors are threaded into the vertebrae and have a reduced diameter leading end which the locking screws expand to lock the anchor in the vertebrae and secure the end of the locking screw in the anchor. The plate has a countersunk cavity including portions overlapping the locking screws. A locking cap fits in the cavity to secure the other end of the locking screws from backing-out of the plate.

12 Claims, 8 Drawing Sheets

U.S. PATENT DOCUMENTS

| | | |
|---|---|---|
| 6,241,731 B1 | 6/2001 | Fiz |
| 6,306,139 B1 | 10/2001 | Fuentes |
| 6,331,179 B1 | 12/2001 | Freid et al. |
| 6,342,055 B1 | 1/2002 | Eisermann et al. |
| 6,383,186 B1 | 5/2002 | Michelson |
| 6,413,259 B1 | 7/2002 | Lyons et al. |
| 6,436,142 B1 | 8/2002 | Paes et al. |
| 6,454,769 B2 | 9/2002 | Wagner et al. |
| 6,454,771 B1 | 9/2002 | Michelson |
| 6,458,133 B1 | 10/2002 | Lin |
| 6,613,053 B1 * | 9/2003 | Collins et al. .................. 606/69 |
| 2002/0151899 A1 | 10/2002 | Bailey et al. |
| 2002/0188296 A1 | 12/2002 | Michelson |

* cited by examiner

BONE FIXATION PLATE

FIELD OF THE INVENTION

This invention relates to the field of orthopedic surgery and, more particularly, to spinal fixation.

BACKGROUND OF THE INVENTION

The use of bone pins and plates for reducing fractures is well known in orthopedic medicine. The pins and plates extend across discontinuities in a bone to fix the broken ends in relation to each other to reduce pain and promote rapid healing without deformity. These devices are secured to the bone by bone screws or nails driven into the bone. More recently, pins, rods, plates and cages have been used to stabilize bone and joints that have deteriorated naturally or as a result of prior trauma. The bone plate of this invention is useful in all these situations.

The interface between the bone screws and the bone presents problems of stability and long term usage that have been addressed in different ways. One of the major problems is usually termed as back-out. This defines the condition in which the screws attaching the plate to the bone loosen over time, either relative to the bone or the plate or both. Severe back-out results in the bone screw working itself out of the bone and/or plate resulting in instability of the bone or joint. This situation results in increasing pain and danger from the instability, as well as, the movement of the screw. There may be several reasons for the back-out but anatomical stresses from body movements contributes greatly to the problem.

Prior art devices address the problem of back-out by use of secondary locking screws that hold the bone screws in the plate. The locking device engages the head of the bone screw and is tightened to fix the screw to the plate and, thus, the bone. Such devices are not particularly suited for deployment on the anterior aspect of the spine because of the close proximity of vital soft tissue organs which dictate a smooth, low profile, contoured surface.

Michelson, U.S. Pat. No. 6,454,771, discloses a bone plate for anterior cervical fixation. The plate has several holes for receiving bone screws. A locking screw mechanism is used to overlay the screw heads.

An expandable insert for placement between vertebrae is disclosed by Paes et al, U.S. Pat. No. 6,436,142. The device is in the nature of a lag screw and can expand with the insertion of an expansion screw.

U.S. Pat. No. 6,342,055 to Eisermann et al discloses a bone plate with bone screws having a snap-in retainer securing the heads to the plate.

Geisler, U.S. Pat. No. 6,231,610, discloses a bone plate with diverging bone screws and serrations on the plate to increase holding power.

U.S. Pat. No. 6,224,602 to Hayes discloses a bone plate with multiple bone screw holes which may be covered by a sliding locking plate. The bone plate has an undercut channel to hold the locking plate in contact with the screw heads. The locking plate is held to the plate by a locking screw once it is slid to the desired position.

Aust et al, U.S. Pat. No. 5,603,713, discloses an anterior lumbar plate attached by screws with various angular connections to the spine.

What is needed in the art is a less complicated system with multiple locking components for added security.

SUMMARY OF THE PRESENT INVENTION

It is an objective of this invention to provide a bone plate, suitable for anterior lumbar fixation, having countersunk screw holes, a low profile in cross section allowing the bone plate to be countersunk into the bone and a smooth distal surface to reduce the possibility of traumatizing adjacent soft tissue during use.

A further objective of the invention is to provide threaded tubular bone anchors embedded in bone guided by the screw holes in the plate. The bone anchors being screwed into the bone by external threads.

Another objective of the invention is to provide locking screws extending through the countersunk screw holes into the bone anchors with the leading ends of the screws expanding the ends of the bone anchors to fix the bone screws to the bone anchors and the anchors to the bone.

Yet another objective of the invention is to provide a bone plate with a locking cap which extends over the area of the countersunk screw holes. The locking cap fits into a large countersunk area of the bone plate covering the countersunk screw holes allowing easy and positive assembly and preventing relative lateral movement between the locking cap and the plate. The locking cap has an aperture and the plate has a receptacle which align when the cap is placed in the countersunk area. A cap screw is threaded into the aligned aperture and receptacle to connect the plate and the cap.

A still further objective of the invention is to provide a kit of several interchangeable components including plates, locking screws, anchors, caps and cap screws to permit the assembly of matching components to fit the anatomy of the patient.

Another objective of the invention is to provide a bone plate system with double headed locking screws and a cam on the bone plate to wedge into the double headed screws.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
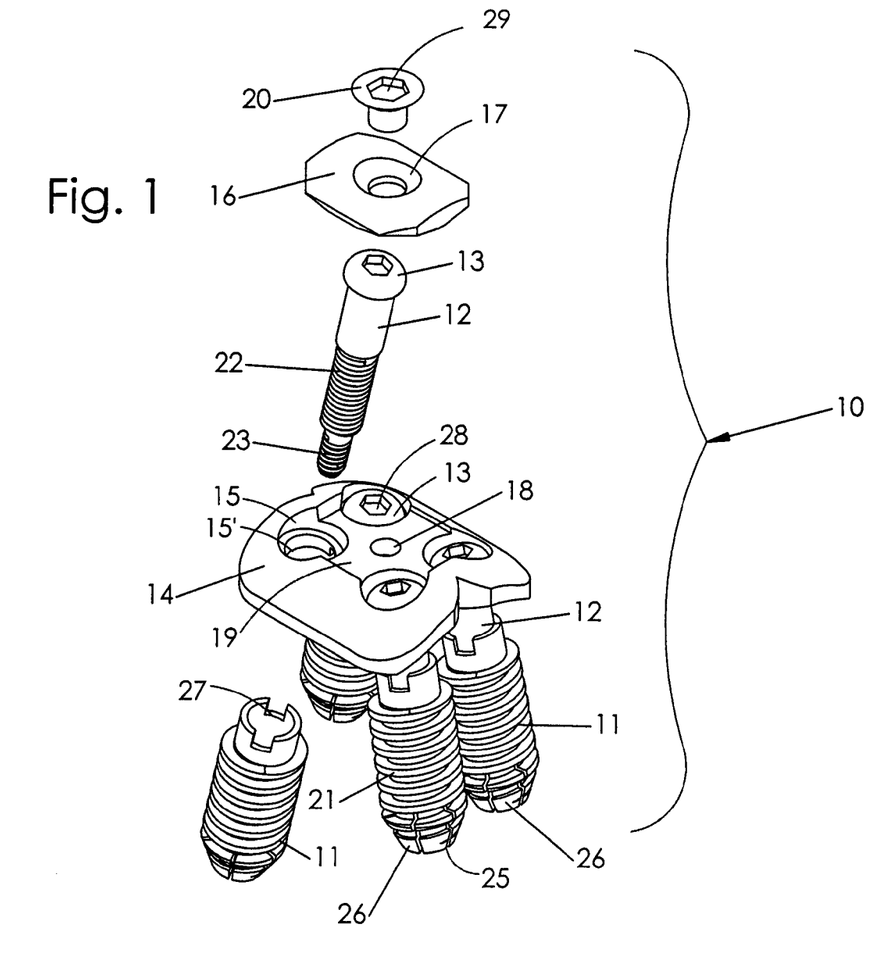
FIG. 1 is an exploded perspective view of the bone plate system of this invention.
Figure 2:
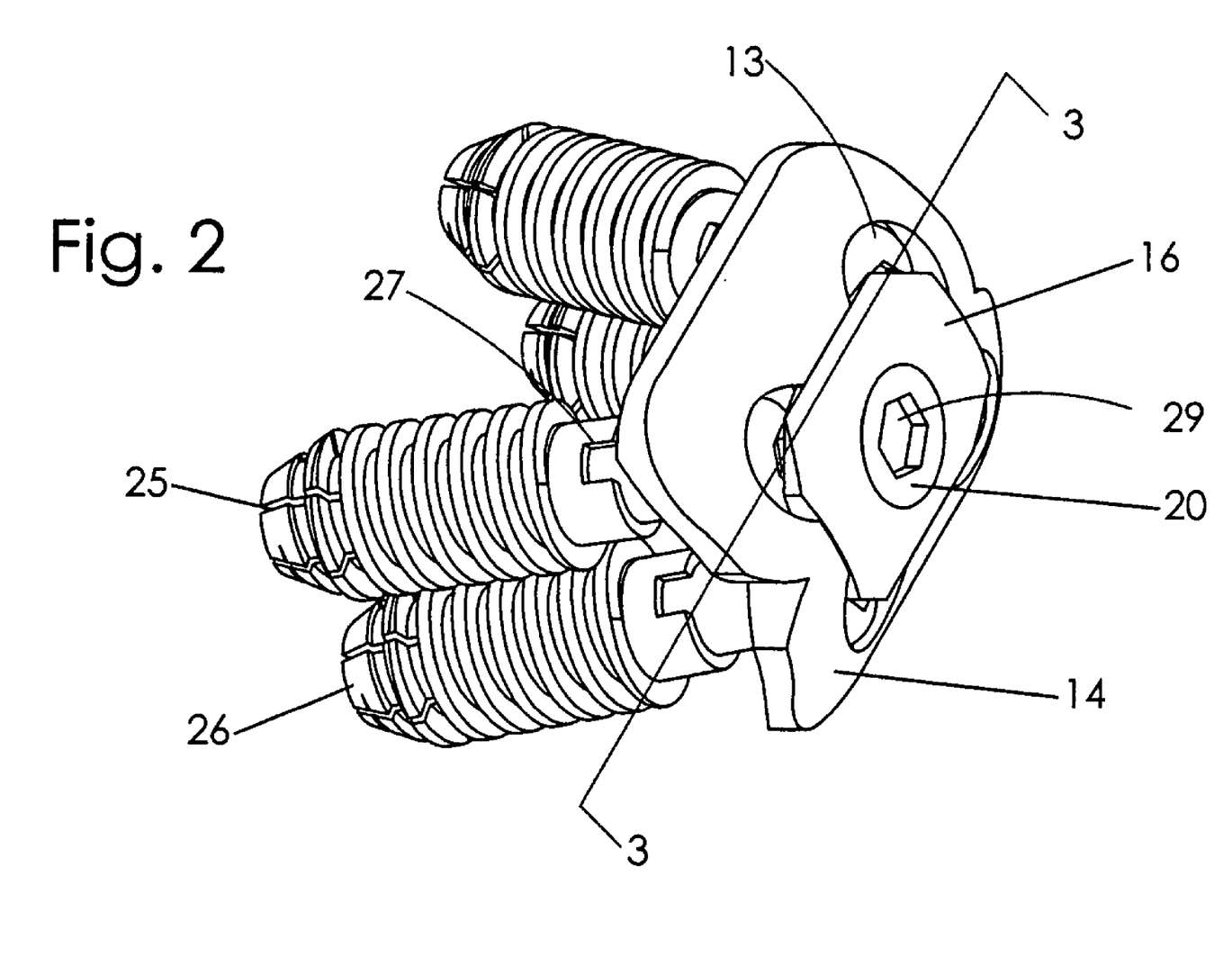
FIG. 2 is a perspective of assembled bone plate system of this invention.
Figure 2A:
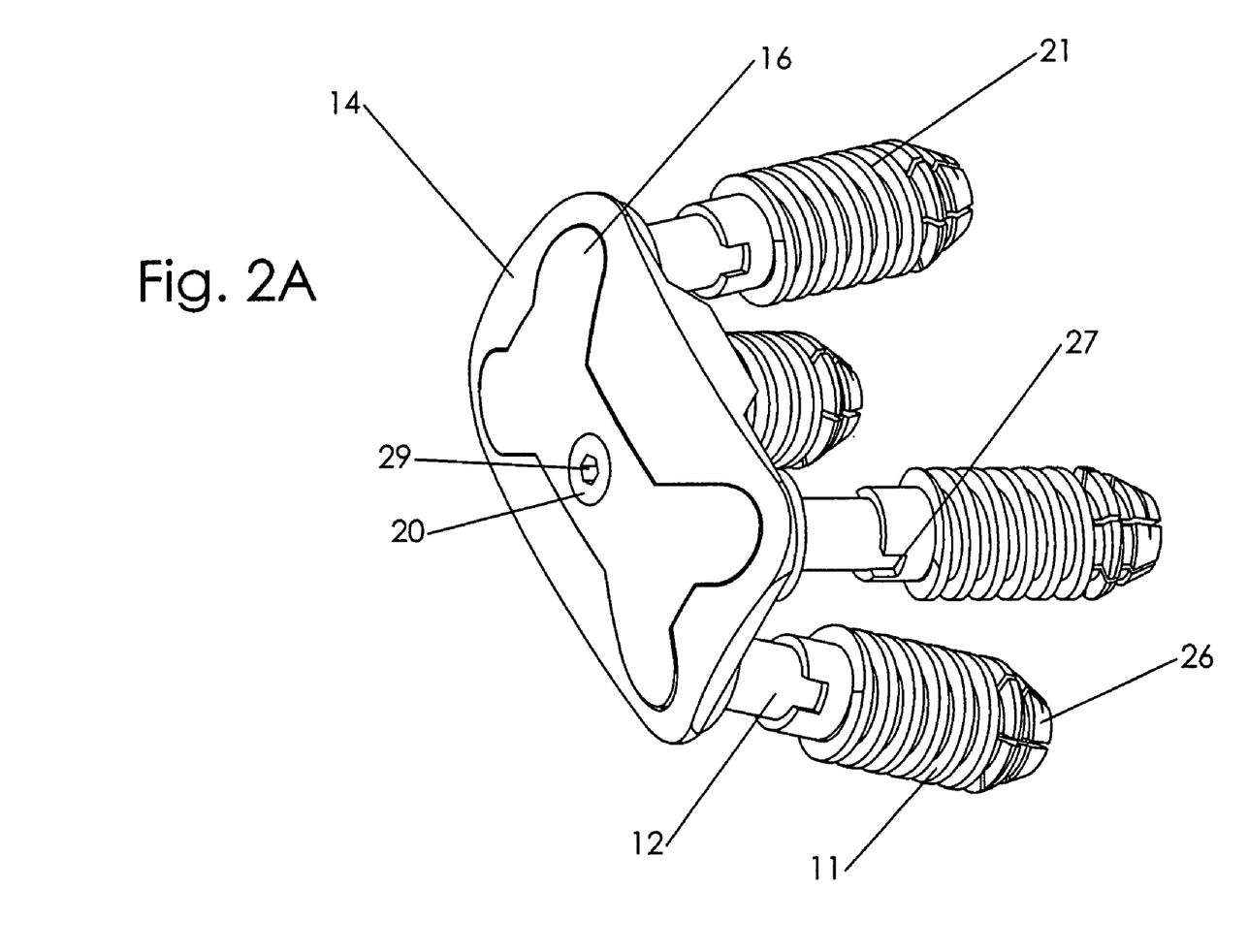
FIG. 2A is a perspective of another embodiment of FIG. 2.
Figure 3:
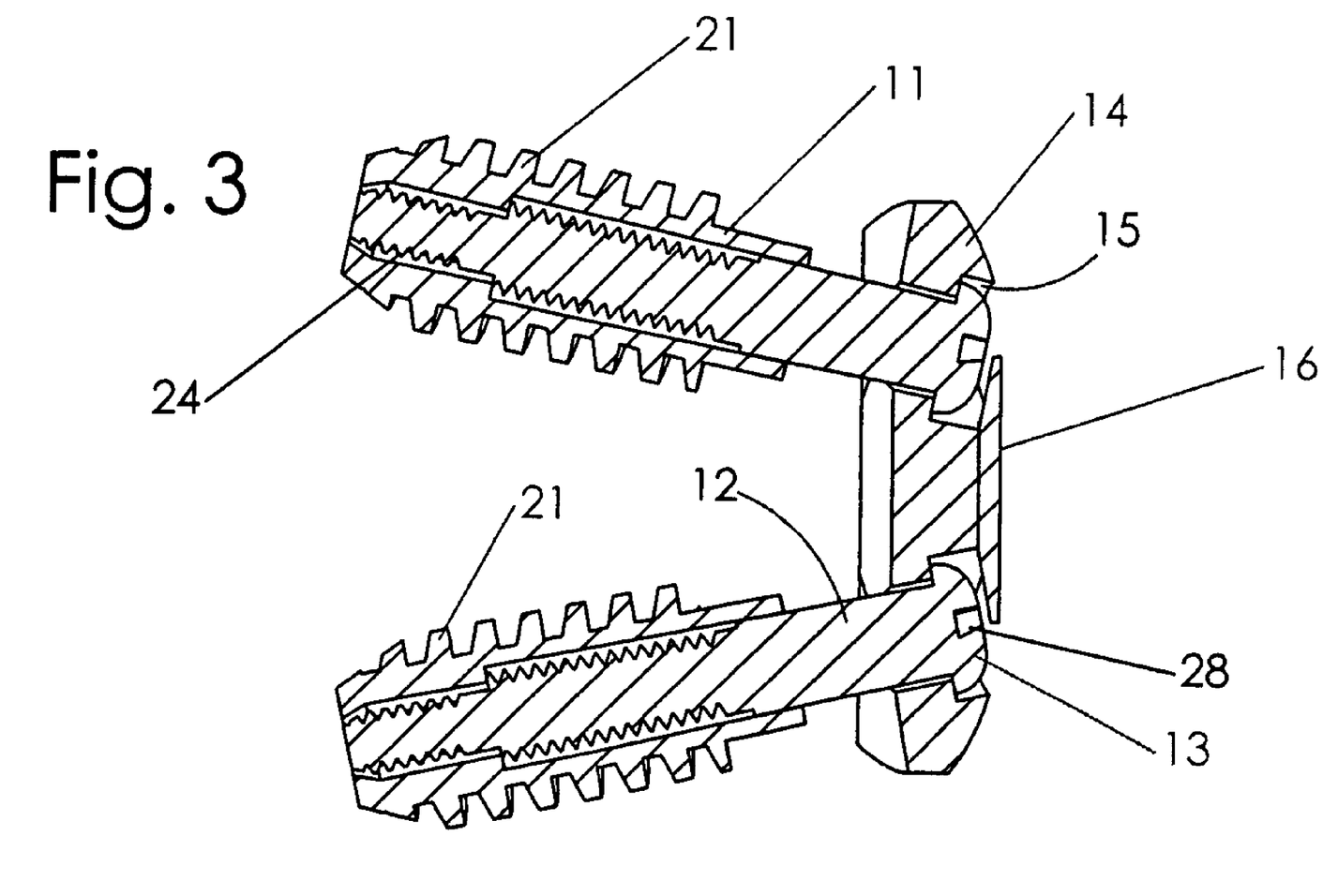
FIG. 3 is a cross section of FIG. 2 along line 3-3.

The bone plate system 10 may be made from any materials having requisite strength and being suitable for use in the body. One complete bone plate system is shown in FIG. 1, FIG. 2 and FIG. 2A though it is understood that several different sizes of interchangeable components may be supplied together as a kit for mixing and matching components to size a system for a particular patient. A kit may have several different sized bone anchors 11 varying in diameter and length with complementary locking screws 12. The different sized locking screws may have the same sized heads 13 to be used in different sized bone plates 14 with screw holes 15' and countersunk depressions 15 of the same size. There may be several different sized locking caps 16, as shown in FIGS. 2 and 2A, to fit into the different complementary sized countersunk areas 19 of the plates while the aperture 17 and the threaded receptacle 18 are of the same size. The locking cap 16 is connected to the plate 14 by a cap screw 20. The kit merely refers to the dissembled components, shown in FIG. 1, that can be assembled to produce an integral whole which corresponds to the anatomical features of a particular patient.

The bone plate system 10 addresses the problem of backout by providing several locking features in the connection of the plate 14 with the bone. These locking features all resist the biomechanical loads placed on the implanted system and result in an aggregate resistance to movement of the components. The locking features are disposed over the length of the plate-bone connection such that the same biomechanical force may not act on all locks simultaneously.

The tubular bone anchors 11 are initially inserted into the bone through pilot holes drilled in the bone or by the use of guide wires. The plate 14 may be used as a guide to align the longitudinal axis of the bone anchors with the longitudinal axis of the countersunk screw holes 15' in the plate. The bone anchors 11 are driven into the bone with a tool (not shown) that engages the slots 27 for rotation of the anchor. The exterior screw threads 21 of the anchor draw the anchor into its seated position in the bone. However, the screw threads 21 produce a mirror image of the toroidal ramp at the bone interface which is a path of least resistance in the opposite direction. The leading or proximal end of the anchor 11 has a number of radial slits 25 through the side wall dividing the proximal circumference into segments 26. Further, the leading end is tapered internally and externally toward a smaller end. This structure of the leading end of the bone anchors 11 creates a change in the bone-anchor interface by expanding, as the locking screws are inserted, to increase the resistance to reverse rotation.

Once the bone anchors 11 are in place, the locking screws 12 are extended through the screw holes 15' of the bone plate 14 with the threads 22 and 23 threadably engaging the interior threads 24 of the bone anchors. The locking screws are rotated by a tool (not shown) fitted into the receptacle 28. As shown, the locking screw 12 has a smooth unthreaded shank near the head 13. An intermediate length of the locking screw has threads 22 to engage the interior threads of the bone anchor. The leading end of the locking screw has a tapered portion with threads 23 to engage the threaded tapered leading end of the bone anchor. The threaded engagement of the locking screws with the leading ends of the anchors and the resultant expansion of the anchors creates a difference in the threading along the interior length of the anchor which resists rotation in the opposite direction. The leading end of the locking screws may be un-threaded and act as a wedge. The locking screw heads 13 are completely enclosed by the depressions 15 and compressively disposed against the bottoms of the depressions. Therefore, the anchor 11 is locked in place by a new bone-anchor interface and the locking screw and anchor are locked together by compression and threading changes. Of course, other combinations of locking screws and anchor configurations may be used, such as, a constant taper of each.

Figure 4:
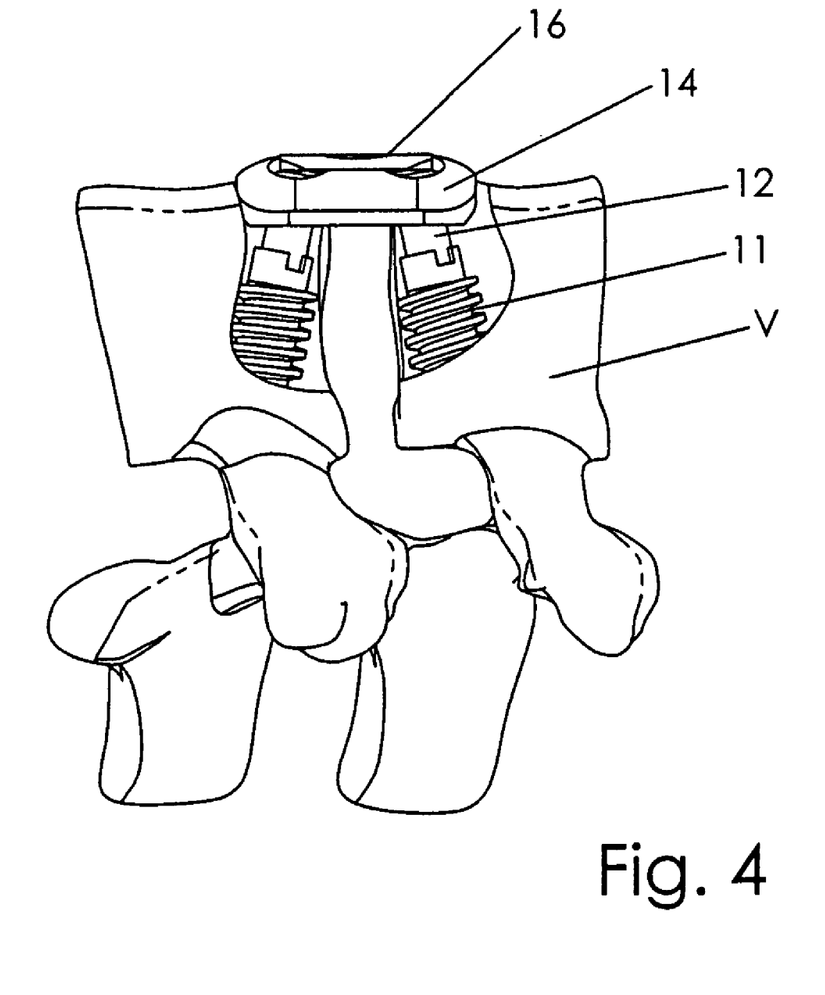
FIG. 4 is a cross section of the bone plate counter sunk into the bone.

After the locking screws 12 have been seated in the bone anchors 11 and depressions 15, the locking cap 16 is placed in the complementary countersink 19 formed in the plate 14. The size and thickness of the locking cap and the size and depth of the countersunk area allow ease of assembly of these components and a resulting low profile with a smooth outer or distal surface. The vertebrae V is shaped to form a counter sunk area in which the plate is placed, as shown in FIG. 4. This is especially important in reducing the possibility of internal trauma to adjacent soft tissue, eg., in the anterior lumbar spinal fixation.

The assembly of the locking plate 16 and the bone plate 14 automatically aligns the receptacle 16 and the aperture 17 for connection by the cap screw 20. The continuous side wall of the enlarged countersunk area and the periphery of the locking cap positively locate the components relative to each other. The cap screw 20 is tightened by a tool (not shown) that fits into receptacle 29. Once the locking cap is secured in place, the heads of the locking screws are prevented from retraction. Because the cap screw 20 is centrally located in the locking cap 16, any reverse rotation of the locking screws is opposed by a leveraging action between the locking cap and the cap screw. This action tends to jam the cap screw and locking cap tighter together.

Figure 5:
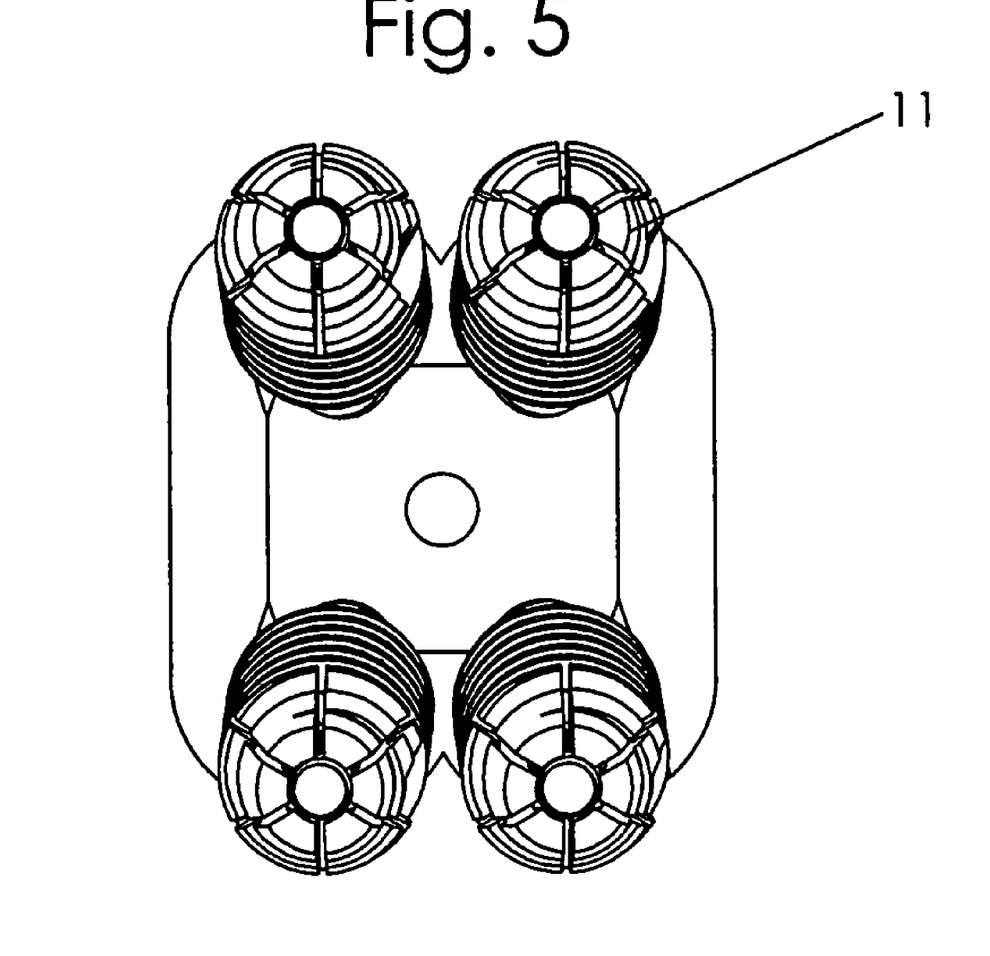
FIG. 5 is a bottom view of the bone plate with the cam rotated into the double headed screws.
Figure 6:
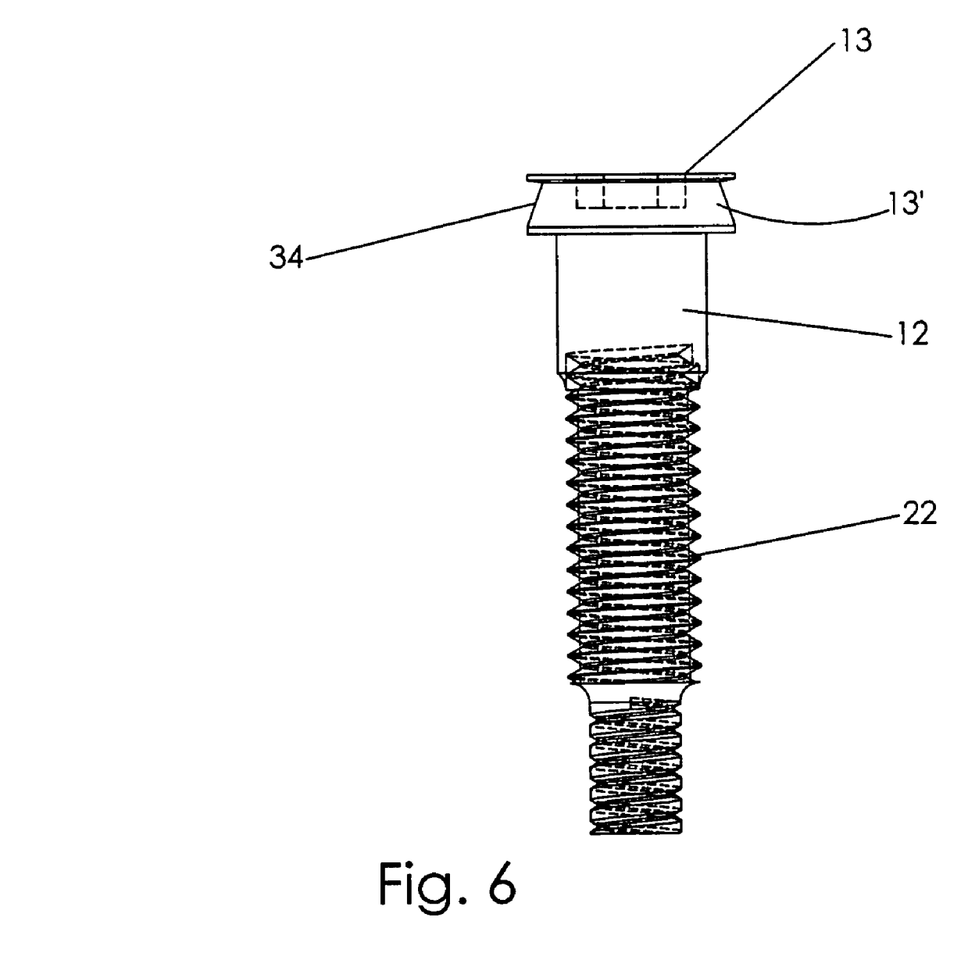
FIG. 6 is a perspective of a double headed locking screw.
Figure 7:
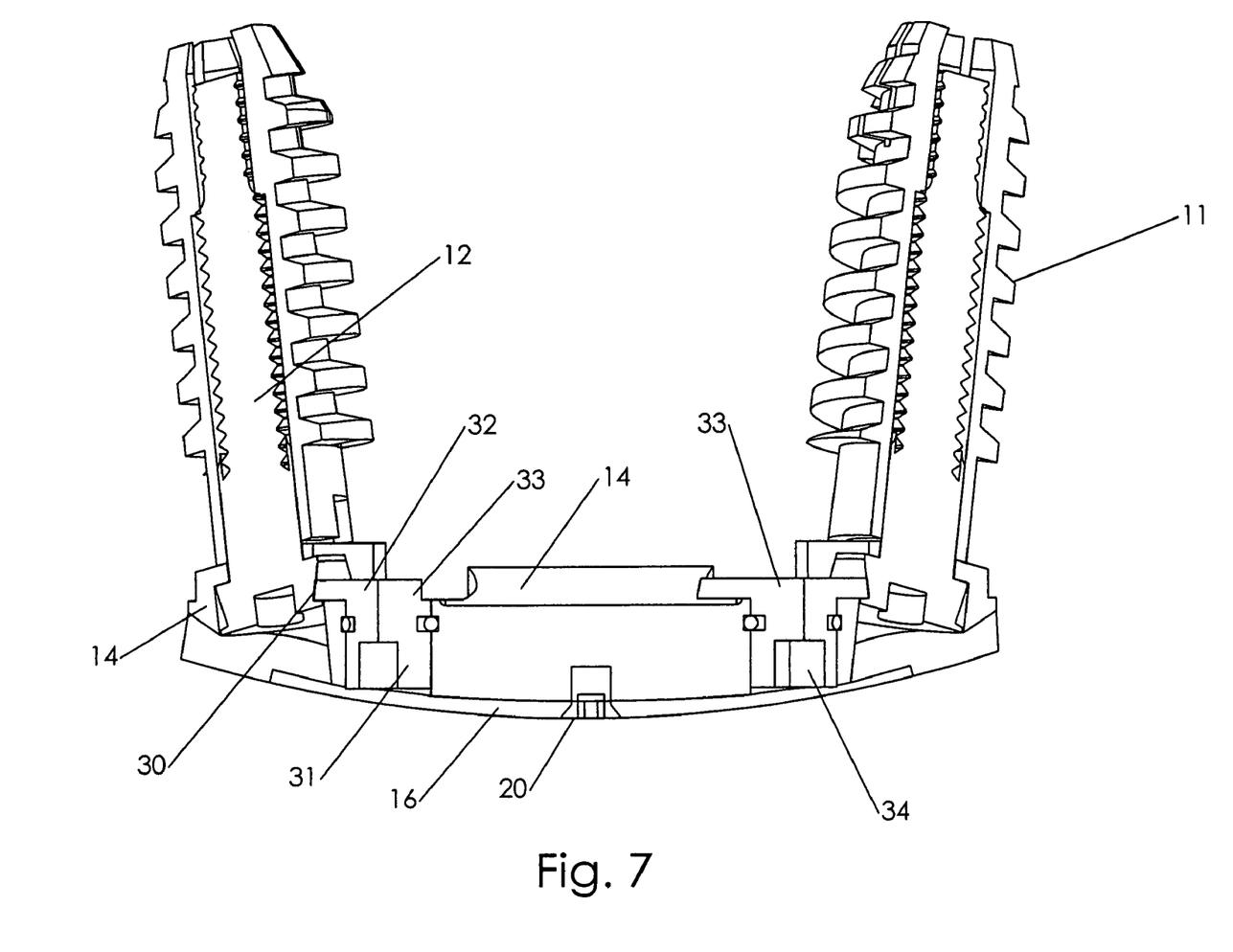
FIG. 7 is a cross section of a bone plate with a double headed screw in place.

As an alternative or additional attachment system is shown in FIGS. 5, 6, and 7. To further secure the locking screws 12 to the plate 14 requires a slit 30 in the side of each of the depressions 15. The slit in each adjacent depression faces the other. A cam 31 is rotatably mounted in the plate 14 between the adjacent depressions and has a flange formed with a blade portion 32 and a brake portion 33. The blade portion 32 will register with the slit 30 in one position and be free of the slit in another position. The brake portion 33 will engage the curved plate when the blade portion is registered with the slit 30 to create a friction stop. In this embodiment, the locking screws have a double headed configuration 13, 13' with a circumferential groove 34 between the two heads. When the locking screws are securely in place in the anchors 11 and plate 14, the grooves 34 will register with the slits 30. The cam 31 extends through the plate 14 into the countersunk portion 19 and is turned by a tool (not shown) to register the blade portion 32 with the slits 30 and the grooves 34. In this position, the brake portion 33 of the flange engages the curved surface of the plate 14. The locking cap 16 may then be applied, as described above. The cams may extend through the locking cap to be tightened along with the cap screw.

The implanted bone plate system results in a positive lock at the proximal ends of the bone anchors and locking screws and an additional lock at the distal end of the locking screws.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. A bone fixation kit for stabilizing skeletal bone across a discontinuity comprising:

a plate having a first end and a second end with an intermediate length to span a discontinuity and a width including at least one screw hole in each of said first end and said second end, said plate including a thickness with a first surface for contacting a bone and an opposite second surface, said plurality of screw holes extending through said thickness for accepting locking screws, said plurality of screw holes each having a first countersink defined by an enlarged depression in said second surface, each said depression having a bottom wall between said first and said second surfaces, each said screw hole and each said depression having a longitudinal axis;

a plurality of locking screws, each locking screw having external threads, each locking screw having adapted to penetrate each of said plurality of screw holes, said locking screws each having an enlarged head adapted to engage said bottom wall of each said depression; and an attachment system having a plurality of tubular bone anchors each having a first end and a second end and interior threads and exterior threads, said interior threads of each of said bone anchors frictionally engaging the external to threads on proximal and distal portions of each of said locking screws whereby said bone anchors are threaded into a bone, wherein said locking screws are inserted through said plate and are threadably engaged with said bone anchors to stabilize the bone across the discontinuity, the length of each locking screw being such that the first surface of said plate is above and spaced from the first end of each of said bone anchors and the distal portion of each locking screw extends into a distal portion of each of said bone anchors when the locking screws are in their final assembled position within the bone anchors, wherein each said plurality of tubular bone anchors has a first internal diameter and a split second end portion with a second internal diameter smaller than said first internal diameter;

wherein the distal portion of each of said plurality of locking screws is threadingly received within the second internal diameter of each of said plurality of bone anchors and;

whereby receipt of each said distal portion within each said split second end portion causes expansion of said split second end portion of each of said plurality of bone anchors.

2. The bone fixation kit of claim 1 wherein said second surface of said plate has a second countersink with a periphery, said periphery including at least a portion of each said enlarged depression of each of said screw holes, said second countersink having a depth, said attachment system in the form of a locking cap adapted to be disposed in said second countersink and shaped to overlay a portion of each said first countersink of each of said screw holes, said locking cap having a first side to contact said plate and an opposite second side, a first threaded aperture in said intermediate length of said plate, a second threaded aperture in said locking cap, and a cap screw adapted to engage said second threaded aperture and said first threaded aperture in to secure said locking cap in said plate.

3. The bone fixation kit of claim 2 wherein said second threaded aperture is countersunk in said second side of said locking cap whereby said cap screw, said second surface of said plate and said second side of said locking cap form a smooth surface without projections whereby said locking screws are fixed in said bone anchors and prevented from backing-out of said plate by said locking cap.

4. The bone fixation kit of claim 1 wherein each of said depressions has sidewalls, a slit in each of said sidewalls, a cam rotatably mounted in said first surface of said plate, said cam having a flange adapted to register with said slit in one position and engage said enlarged head of said locking screw.

5. The bone fixation kit of claim 4 wherein said enlarged head of said locking screw is double headed with a circumferential groove, said flange of said cam adapted to register with said groove.

6. The bone fixation kit of claim 4 wherein said second surface of said plate has a second countersink with a periphery, said periphery including at least a portion of each said enlarged depression of each of said screw holes, said second countersink having a depth, said attachment system in the form of a locking cap adapted to be disposed in said second countersink and shaped to overlay a portion of each said countersink of each of said screw holes, said locking cap having a first side to contact said plate and an opposite second side, a first threaded aperture in said intermediate length of said plate, a second threaded aperture in said locking cap, and a cap screw adapted to engage said second threaded aperture and said first threaded aperture to secure said locking cap in said plate.

7. The bone fixation kit of claim 6 wherein said second threaded aperture in said locking cap is countersunk in said second side of said locking cap whereby said cap screw, said second surface of said plate and said second side of said locking cap form a smooth surface without projections whereby said locking screws are fixed in said bone anchors and prevented from backing-out of said plate by said locking cap.

8. A low profile spinal stabilization system for an anterior lumbar fixation of two adjacent vertebrae comprising a rigid plate having a first end and a second end connected by an intermediate length to span the intervertebral space, said rigid plate having a first surface for contact with vertebrae and an opposite second surface adapted to remain within the plane of the vertebrae, a plurality of holes in said first end and a plurality of holes in said second end, each of said plurality of holes countersunk within a larger depression, a plurality of locking screws engaging said holes, each locking screw having an externally threaded shaft and an enlarged head, said shaft extending through one of said holes and said enlarged head contacting a bottom wall of said depression in one of said holes when locking screw is placed through the plate, and an attachment system having a plurality of tubular bone anchors each including interior threads and exterior threads and a first end and second a end, said interior threads of said bone anchors to frictionally engaging said external threads on proximal and distal portions of each of said locking screws whereby said bone anchors are threaded into a bone, wherein each of said locking screws are inserted through said plate and are threadably engaged with each of said bone anchors and the distal portion of each locking screw extends into a distal portion of each of said bone anchors to stabilize the bone across said intervertebral space, the length of each locking screw is such that the first surface of said plate is above and spaced from the first end of each of said bone anchors when each of the locking screws is in its final assembled position within each of the bone anchors, wherein each of said plurality of tubular bone anchors has a first internal diameter and a split second end portion with a second internal diameter smaller than said first internal diameter;

wherein the distal portion each of said plurality of locking screws is threadingly received within the second internal diameter of each of said plurality of bone anchors;

whereby receipt of each said distal portion within each said split second end portion causes expansion of said split second end portion of each of said plurality of bone anchors.

9. The spinal stabilization system of claim 8 wherein said attachment system includes said plate having a second continuous countersink including at least a portion of each of said plurality of holes, a locking cap having a size commensurate with said second continuous countersink, said locking cap having a first side for contact with said plate and an opposite second side, said locking cap having an aperture therethrough, said aperture countersunk on said second side, a threaded receptacle in said second surface of said intermediate length of said plate, a cap screw having an enlarged head for engaging the countersunk aperture on said locking cap and said threads in said threaded receptacle of said plate whereby when said system is assembled said locking screws are prevented from backing-out of said plate by said locking cap and said second surface of said plate and said second side of said locking cap form a smooth surface without projections.

10. The spinal stabilization system of claim 8 wherein said attachment system includes each of said depressions having sidewalls, a slit in each of said sidewalls, a cam rotatably mounted in said first surface of said plate between said depressions, said cam having a flange adapted to register with said slits in one position and engage said enlarged head of said locking screw.

11. The spinal stabilization system of claim 10 wherein said enlarged head of said locking screw is double headed with a circumferential groove, said flange of said cam adapted to register with said groove.

12. The spinal stabilization system of claim 10 wherein said attachment system includes said plate having a second continuous countersink including at least a portion of each of said plurality of holes, a locking cap having a size commensurate with said second continuous countersink, said locking cap having a first side for contact with said plate and an opposite second side, said locking cap having an aperture there through, said aperture countersunk on said second side, a threaded receptacle in said second surface of said intermediate length of said plate, a cap screw having an enlarged head for engaging the countersunk aperture on said locking cap and said threads in said threaded receptacle of said plate whereby when said system is assembled said locking screws are prevented from backing-out of said plate by said locking cap and said second surface of said plate and said second side of said locking cap form a smooth surface without projections.

* * * * *